(12) United States Patent
Crane et al.

(10) Patent No.: US 9,017,622 B2
(45) Date of Patent: Apr. 28, 2015

(54) CALIBRATOR FOR A SENSOR

(71) Applicant: Lightship Medical Limited, London (GB)

(72) Inventors: Barry Colin Crane, Oxfordshire (GB); William Paterson, Oxfordshire (GB); Nicholas Paul Barwell, Coventry (GB)

(73) Assignee: Lightship Medical Limited, London (GB)

( * ) Notice: Subject to any disclaimer, the term of this patent is extended or adjusted under 35 U.S.C. 154(b) by 0 days.

(21) Appl. No.: 13/686,534

(22) Filed: Nov. 27, 2012

(65) Prior Publication Data

US 2013/0266478 A1  Oct. 10, 2013

Related U.S. Application Data

(60) Provisional application No. 61/622,214, filed on Apr. 10, 2012.

(51) Int. Cl.
*G01N 33/50* (2006.01)
*B01J 19/00* (2006.01)
*A61L 2/08* (2006.01)
(Continued)

(52) U.S. Cl.
CPC ............... *G01N 33/50* (2013.01); *B01J 19/00* (2013.01); *A61L 2/081* (2013.01); *A61B 5/14532* (2013.01); *A61B 5/1459* (2013.01); *A61B 5/1495* (2013.01); *A61B 2560/0223* (2013.01); *A61B 2562/242* (2013.01); *G01N 21/278* (2013.01); *G01N 2021/6484* (2013.01); *G01N 2021/772* (2013.01); *G01N 2021/775* (2013.01); *G01N 2021/7786* (2013.01)

(58) Field of Classification Search
CPC ....................................................... G01N 33/50
USPC ............................................ 422/22, 129, 430
See application file for complete search history.

(56) References Cited

U.S. PATENT DOCUMENTS 4,105,522 A * 8/1978 Friedenberg et al. .... 204/403.01
4,861,728 A    8/1989 Wagner
(Continued)

FOREIGN PATENT DOCUMENTS

CA    1329017    5/1994
EP    1 430 831    6/2004
(Continued)

OTHER PUBLICATIONS

Baldini and Mignani. "Optical-Fiber Medical Sensors," MRS Bulletin, May 2002, 5 pages.
(Continued)

*Primary Examiner* — Sean E Conley
(74) *Attorney, Agent, or Firm* — Fish & Richardson P.C.

(57) ABSTRACT

A calibrator, for calibrating a sensor, has a calibration chamber for containing a calibration liquid. The liquid comprises water or an aqueous solution of an analyte to be sensed. A hydrogen peroxide-quenching material is provided exposed to the interior of the calibration chamber. The hydrogen peroxide-quenching material contacts the calibration liquid. After the calibration chamber containing the calibration liquid is sterilized by irradiation with gamma radiation, the hydrogen peroxide-quenching material decomposes any hydrogen peroxide formed in the calibration liquid to avoid adverse effects on a sensor placed in contact with the calibration liquid.

3 Claims, 2 Drawing Sheets

(51) Int. Cl.
*A61B 5/145* (2006.01)
*A61B 5/1459* (2006.01)
*A61B 5/1495* (2006.01)
*G01N 21/27* (2006.01)
*G01N 21/64* (2006.01)
*G01N 21/77* (2006.01)

(56) References Cited

U.S. PATENT DOCUMENTS

| | | |
|---|---|---|
| 4,889,407 A | 12/1989 | Markle et al. |
| 4,941,308 A | 7/1990 | Grabenkort et al. |
| 5,012,809 A | 5/1991 | Shulze |
| 5,047,627 A | 9/1991 | Yim et al. |
| 5,137,833 A | 8/1992 | Russell |
| 5,185,263 A | 2/1993 | Kroneis et al. |
| 5,482,981 A | 1/1996 | Askari et al. |
| 5,503,770 A | 4/1996 | James et al. |
| 5,511,408 A | 4/1996 | Yoshioka et al. |
| 5,512,246 A | 4/1996 | Russell et al. |
| 5,552,039 A * | 9/1996 | McBrayer et al. ............ 210/90 |
| 6,011,984 A | 1/2000 | Van Antwerp et al. |
| 6,627,177 B2 | 9/2003 | Singaram et al. |
| 6,682,938 B1 | 1/2004 | Satcher et al. |
| 7,253,004 B2 * | 8/2007 | Vossmeyer et al. ........... 436/169 |
| 7,470,420 B2 | 12/2008 | Singaram et al. |
| 8,088,097 B2 | 1/2012 | Markle et al. |
| 8,141,409 B2 | 3/2012 | Crane et al. |
| 2002/0128546 A1 | 9/2002 | Silver |
| 2003/0000834 A1* | 1/2003 | Yoshioka et al. ........ 204/403.01 |
| 2006/0083688 A1 | 4/2006 | Singaram et al. |
| 2006/0108218 A1 | 5/2006 | Gephart et al. |
| 2008/0097288 A1 | 4/2008 | Levin et al. |
| 2008/0188725 A1 | 8/2008 | Markle et al. |
| 2008/0305009 A1 | 12/2008 | Gamsey et al. |
| 2009/0018418 A1 | 1/2009 | Markle et al. |
| 2009/0018426 A1 | 1/2009 | Markle et al. |
| 2010/0280184 A1 | 11/2010 | Crane |
| 2010/0305413 A1 | 12/2010 | Paterson |
| 2011/0044576 A1 | 2/2011 | Crane |
| 2012/0096918 A1 | 4/2012 | Crane et al. |
| 2012/0156793 A1 | 6/2012 | Higgs |

FOREIGN PATENT DOCUMENTS

| | | |
|---|---|---|
| WO | WO00/43536 | 7/2000 |
| WO | WO2007/011691 | 1/2007 |
| WO | WO2008/001091 | 1/2008 |
| WO | WO2009/106805 | 9/2009 |
| WO | WO2009/126942 | 10/2009 |
| WO | WO2011/097586 | 8/2011 |

OTHER PUBLICATIONS

Lindner et al., Design and applications of biomimetic anthraquinone dyes: purification of calf intestinal alkaline phosphates with immobilized terminal ring analogues of C.I. reactive Blue 2, *Journal of Chromatography*, 1989, 473(1) :227-240.

"Optical Glucose Sensor Holds Promise for Diabetics and Intensive Care Patients," ScienceDaily, Mar. 17, 2004 <http://web.archive.org/web/20040404161607/http://www.ScienceDaily.com/releases/2004/03/040317073529.htm> , 6 pages.

Yoon and Czamik. "Fluorescent chemosensors of carbohydrates. A means of chemically communicating the binding of polyols based on chelation-enhanced quenching," *J. Am. Chem. Soc.* 1992, 114:5874-5875.

International Search Report and Written Opinion in International Application No. PCT/GB2013/050860, mailed Jul. 17, 2013, 13 pages.

* cited by examiner

CALIBRATOR FOR A SENSOR

CLAIM OF PRIORITY

This application claims priority under 35 USC §119(e) to U.S. Patent Application Ser. No. 61/622,214, filed on Apr. 10, 2012, the entire contents of which are hereby incorporated by reference.

FIELD

The present disclosure relates to a calibrator for calibrating a sensor, and to a sensor kit including a sensor for detecting an analyte and a calibrator to enable calibration of the sensor. The disclosure also relates to a method of sterilizing a calibrator. In particular embodiments, the invasive or implantable sensors can be maintained in a sterile condition.

BACKGROUND

The usual aim in developing a chemical sensor or biosensor is to produce an electronic signal, which is proportional to the concentration of a specific chemical or set of chemicals (analyte), and with high specificity to the desired analyte. The sensor usually comprises two main components, a chemical or biological part that reacts or complexes with the analyte in question (ideally specifically) to form new chemical or biological products or changes in energy that can be detected by means of the second component, a transducer. The chemical/biological component can be said to act as a receptor/indicator for the analyte. A variety of transduction methods can be used including electrochemical (such as potentiometric, amperometric, conductimetric, impedimetric), optical, calorimetric and acoustic. After transduction the signal is usually converted to an electronic digital signal.

Since the signal generated by the chemical/biological reaction with the analyte is usually dependent not only on the concentration of the analyte but also on the characteristics of the sensor itself, such sensors usually require calibration before they can be utilized quantitatively. The way in which the signal varies with the analyte concentration determines the shape of the calibration curve (signal versus analyte concentration) and may define the number of calibration points. Typical calibration curves can be straight line, exponential, s-shaped etc and the principal of calibration applies to all methodologies of transduction for chemical or biological sensors.

Calibration of sensors with an invasive medical application has its own set of specific issues. Invasive or implantable medical sensors must be presented to the patient in a sterile condition, and are often single use, disposable devices. Ideally, the sensor should be calibrated just before its use because some sensor characteristics that can affect the calibration curve vary with time (ageing effect).

Sterilization of such devices can also provide difficulties. The sterilization process is typically carried out at the point of manufacture to avoid difficulties with poor or incomplete sterilization procedures at a hospital or clinic, and to save time on behalf of the clinician or nurse. Three forms of sterilization are commonly used for the sterilization of medical devices: steam, ethylene oxide, and irradiation.

Steam is usually used for metal surgical instruments, bandages and liquids within containers but is not appropriate for devices with low melting point plastic components or labile chemical or biological components since steam sterilization usually takes place at temperatures above 116 C.

Ethylene oxide sterilization is a surface sterilant that generally does not degrade the receptor and other materials that comprise a sensor, but should only be used to sterilize materials that are free from significant amounts of water, since the ethylene oxide can react with the water to form ethylene glycol. Thus ethylene oxide is the preferred means of sterilizing chemical sensors.

Ethylene oxide sterilization, however, has a number of drawbacks. Firstly, it is usual in sensor construction to immobilize the receptor to the transducer and this is usually achieved by the utilization of polymeric materials. If the sensor is to measure water-soluble analytes, and analytes soluble in blood plasma, the polymeric immobilization material must be hydrophilic (readily adsorb water) to allow the diffusion of the analyte through the immobilization material to the receptor material and allow measurement to take place. To sterilize such a sensor with ethylene oxide, all water must be removed from the hydrophilic material prior to sterilization.

Secondly, to calibrate a sensor that is to measure a water-soluble analyte at the point of use, the user must immerse the sensor in water based solutions of the analyte (or analogues of the analyte) whilst maintaining sterile integrity. However, a calibration vessel, containing calibration solution(s), cannot be sterilized with ethylene oxide, which is a surface sterilant, and therefore must be sterilized by a different process.

Irradiation, usually gamma irradiation, is a penetrating means of sterilization and can therefore sterilize liquids in containers. However, gamma radiation has been found to have an effect on calibration liquids that can adversely affect the operation of analyte sensors.

There is therefore a need for a calibrator, a sensor kit, and a sterilization method that avoids some or any of the above problems.

SUMMARY

A calibrator for calibrating a sensor can include:
a calibration chamber for containing a calibration liquid, said liquid can include water or an aqueous solution; and
an $H_2O_2$-quenching material, exposed to the interior of the calibration chamber, for contacting the calibration liquid.

A sensor kit can include:
a sensor for detecting an analyte, said sensor having a sensing region including a receptor for said analyte; and
a calibrator as defined above.

A method of sterilizing a calibrator having a calibration chamber can include:
providing an $H_2O_2$-quenching material exposed to the interior of the calibration chamber;
providing a calibration liquid in the calibration chamber in contact with the $H_2O_2$-quenching material, said liquid including water or an aqueous solution; and
irradiating the calibrator with gamma radiation.

According to preferred embodiments, the calibrator also includes a lead screw of a mechanism for changing the concentration of an analyte in the calibration liquid. The $H_2O_2$-quenching material can be a coating, preferably of platinum, on the lead screw.

Preferably the analyte is glucose and the sensor is a glucose sensor.

BRIEF DESCRIPTION OF THE FIGURES

Particular embodiments are further described below with reference to an exemplary embodiment and accompanying drawings in which.

DETAILED DESCRIPTION

Sensor

The sensor can be any type of sensor which requires calibration. The calibration devices, systems, kits, and methods described herein can be particularly useful for sensors maintained in a sterile condition. This includes sensors for carrying out in vitro testing, whose accuracy may be affected by increased bacterial counts. For example, bacterial presence can influence the pH of a sensor and therefore affect accuracy. However, the present calibration devices, systems, kits, and methods are particularly useful for invasive or implantable sensors (hereinafter invasive sensors) maintained in a sterile condition during storage and calibration.

Such invasive sensors include sensors for determining a variety of properties, typically properties of blood, although other tissues may also be subject to sensing. Potassium, urea, creatinin and glucose (or other saccharide) sensors are examples of such invasive sensors. The calibration devices, systems, kits, and methods described herein will be described further with reference to a particular type of invasive glucose sensor, but it should be understood that calibration devices, systems, kits, and methods described herein are not limited to such sensors.

Monitoring of patient glucose levels is particularly useful in intensive care units. It has been found that intensive care patients tend to have very high glucose levels. Mortality rates can be significantly reduced merely by maintaining normal glucose levels by administration of insulin. If, however, the patient is administered too much insulin then there is a risk of hypoglycaemia. Intermittent monitoring of glucose is not sufficient to prevent hypoglycaemia since the time from sampling to ascertaining a result is generally too long to accurately determine the current status of a patient, and their response to any administered insulin. Further, in vitro intermittent monitoring significantly increases the workload for the nursing staff due to the frequency of testing required. Invasive devices which provide continuous glucose monitoring are therefore particularly useful in the intensive care environment.

Figure 1:
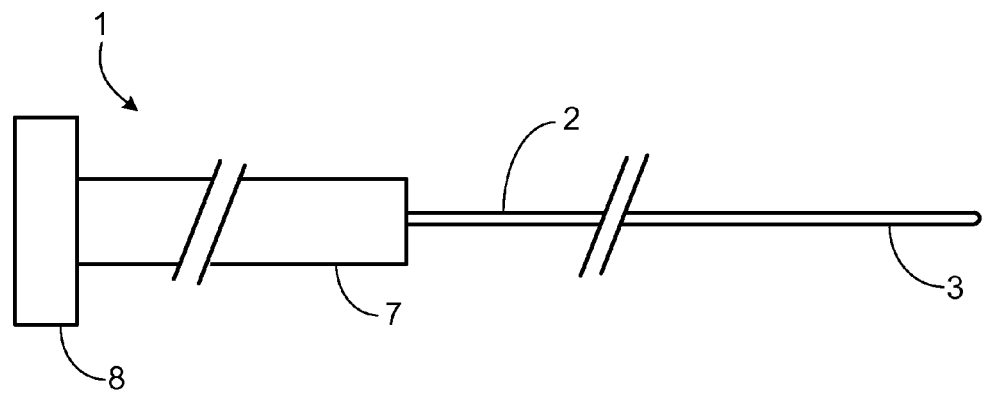
FIGS. 1 and 2 depict an embodiment of a sensor for use in the sensor kit.
Figure 2:
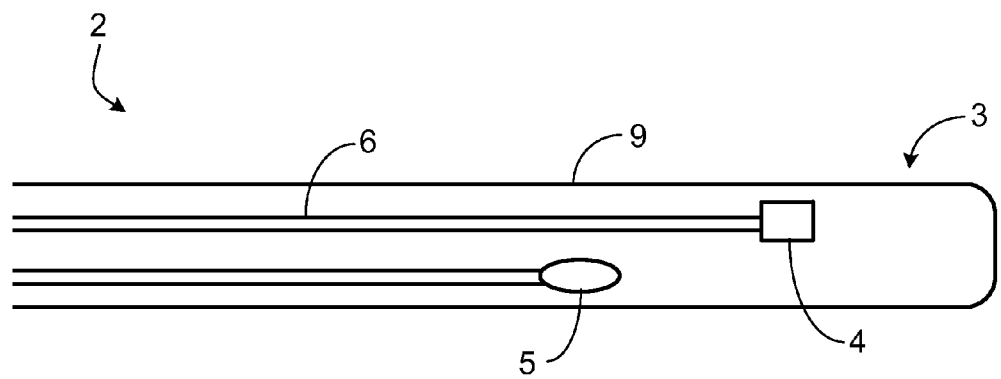

One particular invasive glucose sensor is based on a fiber optic technique and is depicted in FIG. 1. The sensor 1 comprises an insertable tip 2 which is adapted for insertion into a patient, for example insertion into a blood vessel through a cannular. The insertible tip includes a sensing region 3 (depicted in more detail in FIG. 2) in which the glucose receptor 4, and typically also a temperature sensor 5, are positioned. The glucose receptor is immobilized on or in an optical fiber 6, such that a signal emitted by the receptor is transmitted through the optical fiber. The optical fiber extends through cable 7 to connector 8, which is adapted to mate with an appropriate monitor (not depicted). The monitor typically includes further optical cable that mates with the connector at one end and at the other bifurcates to connect to (a) an appropriate light source for the optical sensor and (b) a detector for the emitted signal. Electrical connection to the temperature sensor is also provided through connector 8 and appropriate detection equipment is provided by the monitor.

The sensing region of the sensor is coated with a membrane 9 which should generally be haemocompatible and allow diffusion of glucose (or other analyte where appropriate) from the surrounding blood or body fluid to the receptor 4.

Receptors for a number of analytes which could be incorporated into such a sensor are known in the art. For example, crown ethers may be used to detect potassium. Various enzymes can also be used as a receptor. In the case of glucose, a useful receptor is a boronic acid compound having a fluorophore. The boronic acid species provides the ability to complex with glucose and the fluorescence emission pattern of the molecule is altered in the presence of glucose, which allows optical detection.

The receptor, in some embodiments, is immobilized to the optical fiber in a hydrogel which allows diffusion of water and glucose to the receptor compound. Cross-linked polyacrylamide or polyhydroxyethylmethacrylate (p-HEMA) are examples of hydrogels that can be used.

Calibrator

A calibrator is provided to enable calibration, typically under sterile conditions, of a sensor such as that described above. The calibration chamber within the calibrator provides the means for obtaining two or more sensor readings for calibration solutions of known analyte concentration. The calibration chamber is typically sealed and pre-sterilized and is designed such that calibration can be performed without damaging the seal or sterility of the chamber.

Figure 3:
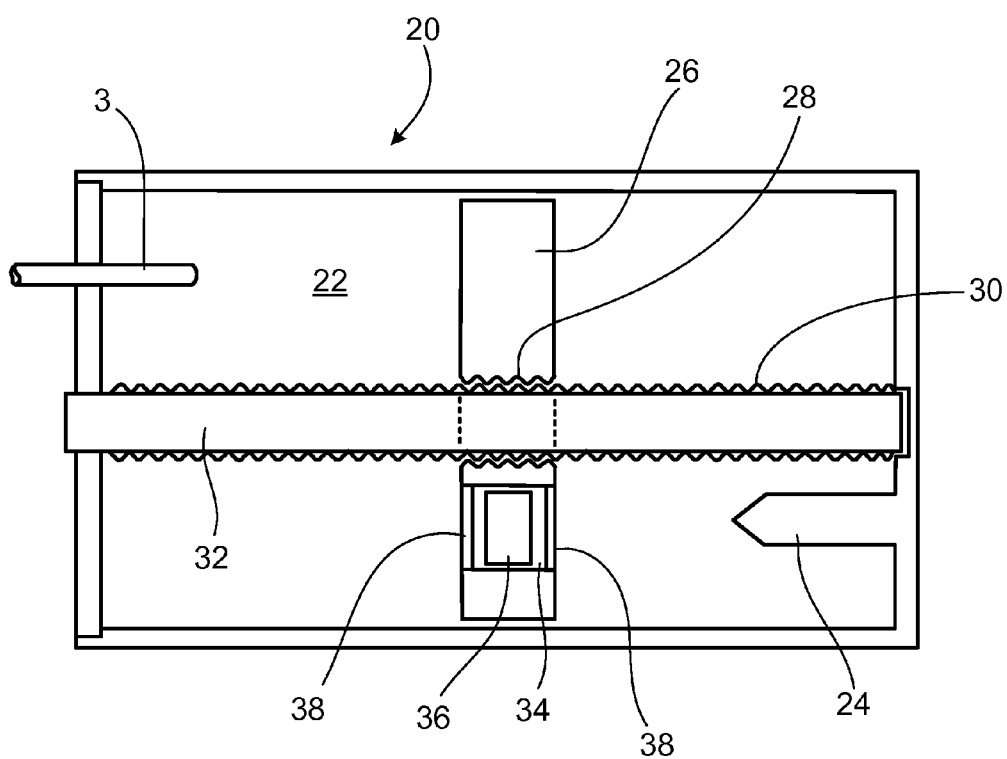
FIG. 3 is a schematic cross-section of a calibrator according to certain embodiments.

An embodiment of a calibrator 20 is illustrated in FIG. 3 in cross-section. The calibrator 20 defines a substantially cylindrical calibration chamber 22. The calibration chamber 22 contains water or an aqueous solution. Initially, the calibration chamber 22 typically contains an isotonic solution and does not contain the analyte. Thus, sensing of the analyte concentration in this state provides a zero reading. However, analyte maybe contained in the initial calibration liquid in the calibration chamber 22, e.g. at low concentration, if desired. Preferably, analyte is only contained in solution initially if it is not degraded by irradiation in the presence of water.

A projection 24 is provided on an end wall of the calibration chamber. An analyte carrier 26 is also provided within the calibration chamber and is splined to the circumferential wall of the calibration chamber 22. The analyte carrier 26 has an inner thread 28 which mates with a thread 30 of a lead screw 32. The lead screw 32 is coaxial with the calibration chamber 22. Thus, rotation of the lead screw 32 results in linear movement of the analyte carrier 26 within the calibration chamber 22 without any rotation of the analyte carrier 26. The analyte carrier 26 is perforate, for example having one or more through-holes (not shown), and/or does not seal around the circumference of the calibration chamber 22, such that calibration liquid within the chamber 22 can pass from one side of the analyte carrier 26 to the other side.

The analyte carrier 26 is provided with a compartment 34 that contains a source of the analyte 36 e.g. glucose. This may be in the form of a constituted solution of the analyte or, as depicted in FIG. 3, the analyte itself in solid form. Where the analyte is glucose, the compartment 34 typically contains glucose in solid form (e.g. power, tablet etc), whilst the calibration chamber 22 initially does not contain glucose. Aqueous solutions of glucose have been found to degrade on sterilization with either heat or gamma radiation. Thus, this preferred embodiment has the advantage that no aqueous solution of glucose is present when the calibrator is sterilized at the time of manufacture. The compartment 34 maybe under inert gas atmosphere (e.g. dry nitrogen) to avoid oxygen-induced irradiation degradation. In the initial condition, depicted in FIG. 3, the compartment 34 is sealed so that the source of analyte 36 is not exposed to the liquid in the calibration chamber 22

Calibration of the sensor can be carried out as follows. The sensing region 3 of the sensor is exposed to the calibration liquid in the calibration chamber 22 as shown in FIG. 3. Various techniques are available for this; for example, the outer wall of the calibration chamber 22 may be designed to be pierced by a needle and the sensor can be inserted into the calibration chamber through or within the needle; alternatively, the sensing region 3 of the sensor may be located in a compartment that communicates with the interior of the calibration chamber 22. The compartment may be sealed from the calibration chamber 22 and the seal only removed when it is the time to perform calibration. Further details of this and other arrangements of the sensor are disclosed in WO 2008/001091 or would be known to the person skilled in the art. Once the sensing region 3 is in contact with the calibration liquid from the calibration chamber 22, a first reading of the sensor output is taken.

Next, the lead screw 32 is rotated (preferably by an electric motor such as a stepper motor) so that the analyte carrier 26 moves linearly within the calibrator 20 (of course the analyte carrier 26 does not rotate because it is splined within the calibration chamber 22). The compartment 34 is sealed from the calibration chamber 22 by dividing material 38. The dividing material 38 can be in the form of a foil, membrane, or fracturable material made of, for example, metals, rubbers, plastics and ceramics. Further information on suitable dividing materials can be gleaned from WO 2008/001091. The lead screw 32 is rotated such that the analyte carrier 26 moves to the right of FIG. 3. This causes the projection 24 to pierce, rupture or break the dividing material 38, thereby releasing the analyte 36 into the calibration chamber 22 where it dissolves in the calibration liquid. Mixing and dissolution can be assisted by reciprocal movement of the analyte carrier 26 by alternately reversing the direction of rotation of the lead screw 32.

Once the content of the compartment 34 is mixed within the calibration chamber 22, this provides a second calibration solution having a greater concentration of analyte than the initial calibration liquid. The sensor reading is again taken which provides a second calibration point. This, along with a predetermined calibration algorithm, enables a calibration curve to be generated and the sensor to be calibrated. The skilled person is familiar with appropriate algorithms for calibrations for any particular type of sensor.

Typically, the calibration is carried out by connecting connection 8 of the sensor to a monitor adapted for continuous measurement of the sensor output. Thus, as soon as the sensor is exposed to the initial calibration liquid of the calibration chamber 22 and the monitor connected and switched on, a first reading can be taken. Rupture or breakage of the dividing material 38 is then carried out and the monitor will continually record the sensor output during mixing of the analyte source with the water or aqueous solution in the calibration chamber 22. The second reading is taken when the sensor output reaches a plateau due to mixing being complete.

The skilled person is able to determine suitable concentrations of analyte for the calibration solutions. Typical concentrations should include zero (first analyte solution) and concentrations at the upper and lower end of those that are likely to be measured by the sensor. In the example of calibration of a glucose sensor for use with intensive care patients, an initial calibration solution typically has a zero concentration, whilst subsequent calibration solutions typically have concentrations of, for example 5 mmolL$^{-1}$ and 10 mmolL$^{-1}$. Alternative concentrations could, however, be selected depending on the type and end use of the sensor. The volume of water or aqueous solution in the calibration chamber 22, and the amount of analyte contained in the first and optionally second and further sources of analyte 36 should be chosen according to the desired final concentrations of the calibration solutions.

When the calibrator 20 is manufactured, it is assembled in the condition with the analyte 36 sealed within the compartment 34 and the calibration chamber 22 filled with the initial calibration liquid. In this condition, the calibrator is sterilized using gamma radiation according to techniques known in the art. However, the present inventors have found that irradiating calibration liquid containing water results in the formation of, amongst other things, hydrogen peroxide ($H_2O_2$). When hydrogen peroxide comes into contact with the sensor, it can affect the sensor chemistry, for example reacting with boronic acids in particular glucose sensors, but not exclusively in this type of sensor. This can result in incorrect sensor readings and so improper calibrations and measurements.

The inventors have also found that gamma irradiation of water generates free radicals that can continue reacting and generating further hydrogen peroxide. The free radicals are stabilized in plastics materials, as may be used in the calibrator, and can keep reacting for extremely long periods of time, even up to 18 months from the time of sterilization. One technique to mitigate this was to shake or agitate the calibrator 20 after irradiation, for a period of time such as 7 days. However, this was not completely effective; it also consumed resources and considerably delayed manufacture of the calibrator 20.

The inventors have alleviated this problem by providing a hydrogen peroxide-quenching material exposed to the interior of the calibration chamber 22 so that it contacts the calibration liquid. In the presently preferred embodiment illustrated in FIG. 3, the hydrogen peroxide-quenching material is in the form of a coating of platinum on the surface of the lead screw 32.

The function of the quenching material is to sequester any hydrogen peroxide in the calibration liquid in the calibration chamber 22 to prevent it coming into contact with the sensor. This can be achieved by locking up, consuming or otherwise decomposing the hydrogen peroxide. In the case of platinum, it catalyzes the decomposition of hydrogen peroxide into water and oxygen. Alternative elements can be used, for example any platinum group metal such as ruthenium, rhodium, palladium, osmium and iridium. Other elements may also be employed, such as gold and silver. Furthermore, mixtures and alloys of any of the above-mentioned elements, for example gold/silver alloys, can be used.

The coating of platinum or other hydrogen peroxide-quenching material can be formed by sputtering, or more correctly, sputter deposition. This is a well-known process, in which ions (for example of an inert gas such as argon) are accelerated into a source of the material to form the coating (such as a piece of platinum). Atoms are ejected from the source which then hit the target (in this case the lead screw 32) and are deposited to form a coating. Sputter deposition equipment is available commercially, or desired articles can be sent to companies to carry out the process commercially.

The thickness of the coating can be extremely small, such as one or a few nanometres. This avoids any interference with the tolerance and operation of the lead screw 32, and is very economical with any precious metals used.

Although the preferred embodiment described above is to coat the lead screw with the hydrogen peroxide quenching material, other items or surfaces could be used. For example, the surface of the analyte carrier 26 or the dividing material 38 for the analyte compartment 34. In particular, the dividing material 38 could be a polymer film that has been metalized, and the metallization could be with the platinum or other quenching material. The hydrogen peroxide quenching material can be adapted to come into contact with the calibration liquid within the calibration chamber 22. A hydrogen peroxide quenching material can also be included in calibrators that do not have a lead screw; examples are disclosed in WO 2008/001019 or are known in the art. However, the lead screw 32 is the currently preferred location for the coating of quenching material because it can be conveniently coated by sputtering before being assembled into the calibrator (it may be inconvenient to sputter onto the internal surface of a calibration chamber), and because it provides a large surface area thereby improving access to the calibration liquid and consequently improving the rate of decomposition of the hydrogen peroxide.

Method

After the hydrogen peroxide quenching material has been provided, such as by forming a platinum coating on the lead screw 32, and the calibrator has been assembled and the calibration chamber filled with the initial calibration liquid (such as water), then the calibrator 20 is irradiated with gamma radiation to sterilize it. Any hydrogen peroxide that is formed as a result, or that is subsequently formed, will be rapidly removed from the calibration chamber by the quenching material, so that when a sensing region 3 of a sensor is introduced into contact with the calibration liquid of the calibration chamber 22 at the time of calibrating the sensor prior to use, contact of hydrogen peroxide with the sensing region is avoided.

Although one specific form of calibrator 20 has been described above with reference to FIG. 3, this is purely an illustrative example. In alternative embodiments, multiple analyte compartments may be provided that can be sequentially ruptured to provide three or more different calibration solutions to provide a greater number of calibration points. Automated calibration can be performed by a suitable equipment that actuates the lead screw 32. Other forms of analyte compartment are envisaged. The calibration chamber can include a heater element and feedback to control the temperature of the calibration liquid. These and numerous other aspects are disclosed in WO 2008/001019 and/or are known to the person skilled in the art and are envisaged for use with the presently described calibration devices, systems, kits, and methods.

Kit

The combination of a sensor for detecting an analyte and a calibrator as described above can be in the form a sensor kit. The sensor and the calibrator of the kit can be placed in a sterile condition in a container that is then sealed and sterilized.

The calibration devices, systems, kits, and methods have been described with reference to various specific embodiments and examples. However, it is to be understood that the claims below are in no way limited to these specific embodiments and examples.

The invention claimed is:

1. A calibrator for calibrating a sensor, comprising:
   a calibration chamber for containing a calibration liquid, said liquid comprising water or an aqueous solution;
   an $H_2O_2$-quenching material, exposed to an interior of the calibration chamber, for contacting the calibration liquid; and
   a lead screw of a mechanism for changing the concentration of an analyte in the calibration liquid, and wherein the $H_2O_2$-quenching material is a coating on the lead screw.

2. A sensor kit comprising:
   a sensor for detecting a saccharide, said sensor having a sensing region comprising a receptor for said saccharide; and
   a calibrator including a sealed calibration chamber containing a calibration liquid and an $H_2O_2$-quenching material on an interior surface of the calibration chamber for contacting the calibration liquid, said liquid comprising water or an aqueous solution.

3. A sensor kit according to claim 2, wherein the sensor is a glucose sensor and the saccharide is glucose.

\* \* \* \* \*